US005925673A

United States Patent [19]
Hellberg et al.

[11] Patent Number: 5,925,673
[45] Date of Patent: Jul. 20, 1999

[54] BENZOFURANS AND BENZOPYRANS AS CYTOPROTECTIVE AGENTS

[75] Inventors: Mark R. Hellberg, Fort Worth; Abdelmoula Namil, Arlington; Jon C. Nixon, Mansfield, all of Tex.

[73] Assignee: Alcon Laboratories, Inc., Fort Worth, Tex.

[21] Appl. No.: 08/994,115

[22] Filed: Dec. 19, 1997

Related U.S. Application Data

[63] Continuation-in-part of application No. 08/849,230, Jun. 4, 1997, Pat. No. 5,811,438, which is a continuation-in-part of application No. 08/362,718, Dec. 23, 1994, Pat. No. 5,607,966, which is a continuation-in-part of application No. 08/472,445, Jun. 7, 1995, Pat. No. 5,643,943.

[51] Int. Cl.$^6$ .......................... A61K 31/36; A61K 31/35
[52] U.S. Cl. .......................... 514/465; 514/456; 549/407; 549/437
[58] Field of Search .................................. 514/456, 465; 549/407, 437

[56] References Cited

U.S. PATENT DOCUMENTS

| | | | |
|---|---|---|---|
| 4,645,845 | 2/1987 | Gehrken et al. | 549/407 |
| 5,484,810 | 1/1996 | Grisar et al. | 514/456 |
| 5,607,966 | 3/1997 | Hellberg et al. | 549/407 |
| 5,643,943 | 7/1997 | Gamache et al. | 514/456 |
| 5,811,438 | 9/1998 | Hellberg et al. | 514/458 |

FOREIGN PATENT DOCUMENTS

| | | |
|---|---|---|
| 0 387 771 A2 | 9/1990 | European Pat. Off. . |
| 64-40484 A2 | of 1989 | Japan . |

OTHER PUBLICATIONS

Bellavite, P., "The Superoxide–Forming Enzymatic System Of Phagocytes", *Free Radical Biology & Medicine*, vol. 4, pp. 225–261 (1988).

Bonne, C. et al., 2–(2–Hydroxy–4–methylphenyl)aminothiazole Hydrochloride as a Dual Inhibitor of Cyclooxygenase/Lipoxygenase and a Free Radical Scavenger, *Drug Research*, vol. 39(II), No. 10, pp. 1242–1250 (1989).

Campbell, W., "Lipid–Derived Autacoids: Eicosanoids And Platelet–Activiating Factor", *Goodman and Gilman's The Pharmacological Basis of Therapeutics*, Pergman Press, NY, pp. 600–617 (1990).

Carew, *Proceedings of the National Academy of Science*, U.S.A., vol. 84, pp. 7725–7729 (1989).

Cherfan, G.M., et al., Nuclear Sclerotic Cataract After Vitrectomy for Idiopathic Epiretinal Membranes Causing Macular Pucker, *American Journal Of Ophthalmology*, vol. 111, pp. 434–438 (1991).

Chow, C., "Vitamin E And Oxidative Stress", *Free Radical Biology & Medicine*, vol. II, pp. 215–232 (1991).

Dobbs, R.E., et al., *Evaluation Of Lens Changes In Idiopathic Epiretinal Membrane*, vol. 5, Nos. 1 & 2, pp. 143–148 (1988).

Duchstein, H. et al., "Activated Species of Oxygen: A Challenge to Modern Pharmaceutical Chemistry", *Archives of Pharmacology*, vol. 325, pp. 129–146 (1992).

Duniec, Z. et al.; "Antioxidant properties of some chemicals vs their influence on cyclooxygenase and lipoxidase activities", *Biochemical Pharmacology*, vol. 32, No. 14, pp. 2283–2286 (1983).

Gifford, H., "On The Treatment Of Sympathetic Ophthalmia By Large Doses Of Salicylate Of Sodium, Aspirin, Or Other Salicylic Compounds", *Ophthalmoscope*, vol. 8, pp. 257–259 (1910).

Guo, A., et al., Effects of anti–inflammatory and immunosuppressive drugs on the heterolamellar corneal transplantation in rabbits, *Current Eye Research*, vol. 9, No. 8, pp. 749–757 (1990).

Halliwell et al., "[1] Role of Free Radicals and Catalytic Metal Ions in Human Disease: An Overview", *Methods in Enzymology*, vol. 186, pp. 1–85 (1990).

Insel, P., "Analgesic–Antipyretics And Antiinflammatory Agents: Drugs Employed In The Treatment Of Rheumatoid Arthritis And Gout", *Goodman and Gilman's The Pharmacological Basis of Therapeutics*, Pergman Press, NY, pp. 638–669 and 681 (1990).

Kreiger, A.E., Wound Complications In Pars Plana Vitrectomy, *Retina*, vol. 13, No. 4, pp. 335–344 (1993).

Lindstrom, R.L., et al., Corneal Preservation at 4° C. with Chondroitin Sulfate–Containing Medium, *The Cornea: Transactions of the World Congress on the Cornea III*, edited by H. Dwight Cavanagh, Raven Press, Ltd., New York, Chapter 14, pp. 81–89 (1988).

Momsen, W. et al., "Lipid Structural Reorganization Induced by the Pancreatic Lipase Cofactor, Procolipase", *Biochemistry*, vol. 34, pp. 7271–7281 (1995).

Nelson, P., "Cyclooxygenase Inhibitors", *CRC Handbook of Eicosanoids: Prostaglandins and Related Lipids, vol. II, Drugs Acting Via the Eicosanoids*, CRC Press, Boca Raton, FL, pp. 59–133 (1989).

Parinandi et al., *Arch Biochem Biophys*, vol. 28, pp. 45–52 (1990).

Petty, M., et al.; "Protective effects of an α–tocopherol analogue against myocardial reperfusion injury in rats", *European Journal of Pharmacology*, vol. 210, pp. 85–90 (1992).

PJB, Scrip No., 1574:31 (1990).

Rainsford, K.D., editor, *Inflammation and Mechanism and Actions of Traditional Drugs, vol. 1 Anti–inflammatory and Anti–rheumatic drugs*, Boca Raton, FL, CRC Press, pp. 54–68, 79–87, 120–126 and 140–144 (1985).

(List continued on next page.)

*Primary Examiner*—Amelia Owens
*Attorney, Agent, or Firm*—Michael C. Mayo

[57] ABSTRACT

Methods for treating inflammnatory pathologies are disclosed. Particularly, the methods utilize pharmaceutical compositions containing certain compounds having an anti-inflanumatory and anti-oxidant moiety covalently linked by thiol or sulfoxide or sulfone bond. The compounds are useflil in preventing and treating inflammatory disorders through several mechanisms.

39 Claims, No Drawings

OTHER PUBLICATIONS

Stampfer, M., et al.; "Vitamin E Consumption and the Risk of Coronary Disease in Women", *New England Journal of Medicine,* vol. 328, No. 20, pp. 1444–1449 (1993).

Steinberg, D., et al.; "Lipoprotein and Atherogenesis", *JAMA,* vol. 264, No. 3, pp. 3047–3052 (1990).

Rimm, E., et al.; "Vitamin E Consumption and the Risk of Coronary Heart Disease in Men", *New England Journal of Medicine,* vol. 328, No. 20, pp. 1450–1456 (1993).

Smaby, J. M., et al., "Characterization of Lipid Miscibiity in Liquid–Expanded Monolayers at the Gas–Liquid Interface", *Langmuir,* vol. 8, No. 2, pp. 563–570 (1992).

Sies, H., et al.; "Role of tocopherols in the protection of biological systems against oxidative damage", *Journal of Photochemistry and Photobiology,* vol. 8, pp. 211–224 (1991).

Thompson, J.T., et al., Progression of Nuclear Sclerosis and Long–term Visual Results of Vitrectomy With Transforming Growth Factor Beta–2 for Macular Holes, *American Journal Of Ophthalmology,* vol. 119, pp. 48–54 (1995).

Vane, J., et al., "Inflammation and the mechanism of action of anti–inflammatory drugs", *FASEB Journal,* vol. 1, pp. 89–96 (1987).

BENZOFURANS AND BENZOPYRANS AS CYTOPROTECTIVE AGENTS

The present application is a continuation-in-part of 08/849,230, filed Jun. 4, 1997, now U.S. Pat. No. 5,811,438 which is a continuation-in-part of U.S. Pat. application Ser. No. 08/362,718, filed Dec. 23, 1994, now U.S. Pat. No. 5,607,966 and U.S. Pat. application Ser. No. 08/472,445, filed on Jun. 7, 1995 now U.S. Pat. No. 5,643,943.

BACKGROUND OF THE INVENTION

The present invention is directed to the provision of compounds having potent anti-proliferative and anti-oxidant activity. The invention is further directed to compositions containing the compounds of the present invention for use in pharmaceutical applications. The present invention is also directed to various methods of using the compounds and compositions of the present invention in pharmaceutical applications including: 1) the treatment of inflammatory disorders including ocular inflammation associated with ophthalmic disease and ophthalmic surgery; 2) the prevention of corneal haze following ocular surgery; 3) tissue preservation including cornea preservation during transplantation procedures; and 4) as an adjunct to heart disease therapy. These compounds may find special utility in ocular indication such cataract formation following ocular surgery including secondary cataract following IOL implantation, cataract formation associated with chronic uveitis, reduction in the rate of regression of correction following laser surgery to correct vision defects, regrowth of pterygium following removal, arresting the rate of neovascularization caused by conditions such as diabetic retinopathy, or the wet form of macular degeneration. Systemic application of this compound might reduce the formation and rate of progression of atherosclerotic lesion or other vascular inflammatory pathologies.

Inflammation from cellular stress can cause excessive tissue damage. Numerous biochemical pathways are known to lead to inflammation. In general, the cyclooxygenase system produces prostaglandins, while the lipoxygenase system produces leukotrienes, "HETES" and "HPETEs". Such agents have been associated with inflammation. See generally, *Goodman and Gilman's The Pharmacological Basis of Therapeutics*, pages 600–617, Pergman Press, NY (1990). Therapies designed to inhibit the production of these types of agents are therefore of great interest.

Non-steroidal anti-inflammatory agents ("NSAIA") have been used for the treatment of inflammatory disorders. The following references may be referred to for further background concerning this use of NSAIAs:

*Ophthalmoscope*, volume 8, page 257 (1910);

*Nature*, volume 231, page 232 (1971);

*FASEB Journal* volume 1, page 89 (1987); and

*Inflammation and Mechanisms and Actions of Traditional Drugs*, Vol. I

Anti-inflammatory and Anti-rheumatic drugs. Boca Raton, FL, CRC Press, (1985).

However, there are some problems associated with NSAIA treatment including delivery to the appropriate site of action and side effects (*Goodman and Gilman's The Pharmacological Basis of Therapeutics*, pages 638–669, Pergman Press, NY (1990)).

Free radical molecules also play a major role in inflammation. These unstable chemical moieties lead to the oxidation of tissue resulting in damage. Such oxidative stress and damage has been described in *Biochemical Pharmacology*, 32(14), 2283–2286 (1983) and *Free Radicals in Biology and Medicine*, 4, 225–261 (1988). Agents that act as anti-oxidants can protect against oxidative damage. Such protection has been the subject of numerous scientific publications, including the following:

*Archives of Pharmacology*, volume 325, pages 129–146 (1992);

*Journal of Photochemistry and Photobiology*, volume 8, pages 211–224 (1991);

*Free Radicals in Biology and Medicine*, volume 11, pages 215–232 (1991); and

*European Journal of Pharmacology*, volume 210, pages 85–90 (1992).

The combination of anti-oxidant activity with other pharmacologically significant activities in a single molecule is discussed in JP 010484 A2 and EP 387771 A2; and compounds with cyclooxygenase/5-Lipoxygenase and anti-oxidant activity are discussed in *Drug Research*, 39(II) Number 10, pages 1242–1250 (1989). However, these references do not disclose the compounds of the present invention.

Ocular inflammation is a condition which generally affects the patient with scratchiness, itchiness and/or red eye. Ocular inflammation can be initiated by various insults. For example, ocular inflammation can result from allergic response to various allergens, trauma to the eye, dry eye and surgical complications. Various anti-inflammatory therapies are currently in use for the treatment of ocular inflammation including the topical administration of diclofenac.

Ocular surgery can result in various post-surgical complications to the eye. Such complications generally include: 1) loss of vascular blood barrier frinction; 2) tissue edema including conjunctiva swelling, conjuctiva conjestion and comneal haze; 3) cataract formation; and 4) loss of membrane integrity including decrease in docosahexanenoic acid levels in membrane phospholipids.

As stated above, vitrectomy surgery can induce a variety of post-surgical complications. Many of these complications are further potentiated in diabetic patients who are at risk for many ocular pathologies. Posterior segment surgery due to the severity of the surgical procedure can cause extensive tissue damage at both the acute and chronic phases of the recovery process. The acute phase of the postsurgical period is characterized by both ocular neovascularization and tissue edema. This is caused by breakdown of the blood aqueous and blood retinal barrier functions resulting in sustained vascular permeability following the surgical trauma. The presence of elevated inflammatory and serum factors induce cell proliferation during the normal wound healing process. Slitlamp clinical examinations at 24 hours have indicated extensive anterior chamber flare and cell influx, conjunctiva congestion and swelling (with discharge), iritis, and corneal haze. See for example, Kreiger, A. E., *Wound Complications In Pars Plana Vitrectomy, Retina,* volume 13, No. 4, pages 335–344 (1993); Cherfan, G. M., et al., *Nuclear Sclerotic Cataract After Vitrectomy for Idiopathic Epiretinal Membranes Causing Macular Pucker, American Journal Of Ophthalmology,* volume 111, pages 434–438 (1991); Thompson, J. T., et al., *Progression of Nuclear Sclerosis and Long-term Visual Results of Virectomy With Transforming Growth Factor Beta-2 for Macular Holes, American Journal Of Ophthalmology,* volume 119, pages 48–54 (1995) and Dobbs, R. E., et al., *Evaluation Of Lens Changes In Idiopathic Epiretinal Membrane,* volume 5, Nos. 1 & 2, pages 143–148 (1988).

The chronic phase of the postsurgical period is characterized by more severe complications that can necessitate additional surgery. These include an incidence of recurrent retinal detachment, epiretinal proliferation, neovascular glaucoma, corneal problems, vitreous hemorrhage, rate of cystoid macular edema, and occurrence of cataract formation within six months of surgery.

The frequency of these complications can be lessened by facilitating the recovery of vascular leakage and limiting the duration of the cellular proliferative response by introduction of therapeutic compounds into the irrigating solution during the time of surgery.

Organ or tissue tranplantation requires the preservation of the tissue from the time of excission from the donor to the time of transplantation into the recipient. During this time the tissue can become inflammed and even die. Methods of preserving the tissue have included the use of various temperature conditions, the use of chondroitin sulfate and the use of anti-inflammatory agents (Lindstrom, R. L., et al., *Corneal Preservation at 4° C. with Chondroitin Sulfate-Containing Medium, The Cornea: Transactions of the World Congress on the Cornea III*, edited by H. Dwight Cavanagh, Raven Press, Ltd., New York, Chapter 14, pages 81–89 (1988); and Guo, A., et al., *Effects of anti-inflammatory and immunosuppressive drugs on the heterolamellar corneal transplantation in rabbits, Current Eve Research*, volumne 9, No. 8, pages 749–757 (1990)).

Oxidation of various biomolecules in the vasculature has been implicated in numerous cardiovascular pathologies including atherosclerosis, thrombosis, myocardial infarction and congestive heart failure. In particular, several reports demonstrate a correlation between the oxidation of low-density lipoproteins (LDL) and the progression of atherosclerotic lesions (*New England Journal of Medicine*, volume 328(20), pages 1444–1449 (1993)). These oxidized LDLs have been furher characterized in several pathological events including: 1) chemotaxis, which draws monocytes to the afflicted tissue; 2) differentiation of mdnocytes into macrophages; 3) uptake of LDL by macrophages to form foam cells; 4) proliferation of smooth muscle cells; 5) development of atherosclerotic lesions; and 6) cytotoxic effects on endothelial cells as well as increases in arterial vasoconstriction (*JAMA*, volume 264(3), pages 3047–3052 (1990)).

The use of antioxidants to ameliorate coronary heart disease has been explored. Epidemiological studies have correlated the dietary intake of Vitamin E with reduced risk to coronary heart disease (*New England Journal of Medicine*, volume 328(20), pages 1444–1449 (1993); and *New England Journal of Medicine*, volume 328(20), pages 1450–156 (1993)). β-carotene, a naturally occuring antioxidant, has been pursued in the clinic for cardiovascular disease indications (Scrip No., 1574:31 (1990)). Additionally, research has shown that treatment of hypercholesterolemic animals with antioxidant drugs, including the phenolic antioxidant compound, probucol, has reduced the development of atherosclerosis (*Proceedings of the National Academy of Science*, U.S.A., volume 84, pages 7725–7729 (1989)).

Oxygen radicals have also been implicated in the pathogenesis of a number of other inflammatory conditions. Such conditions have included stroke, rheumatoid arthritis, retinopathy and endotoxic liver injury. It is believed that anti-oxidants would be useful in treating such conditions (*Methods in Enzymology*, volume 186, pages 1–85 (1990)).

Anti-inflammatory therapy has been suggested as an adjuvant to the treatment of various cardiovascular indications. These agents assist in preventing thrombotic and atherosclerotic occlusions and restenosis of the vasculature by inhibiting platelet and leukocyte aggregation.

As such, aspirin has been prescribed broadly, for anti-inflammatory and analgetic indications, as well as for patients with unstable angina. Ibuprofen and naproxen have been prescribed for treatment of rheumatoid arthritis and moderate pain. However, there are some problems associated with NSAIA treatment including delivery to the appropriate site of action and side effects (*Goodman and Gilman's The Pharmacological Basis of Therapeutics*, pages 638–669, Pergman Press, NY (1990)).

The present invention is directed to the provision of new compounds that have potent anti-inflammatory, anti-proliferative and anti-oxidant activity in a single molecule. The use of a single chemical entity with these potent activities provides increased protection relative to the use of a compound with singular activity. The use of a single agent having both activities over a combination of two or three different agents provides uniform delivery of an active molecule, thereby simplifying issues of drug metabolism, toxicity and delivery.

SUMMARY OF INVENTION

The present invention provides methods of using novel compounds having potent anti-inflammatory, anti-proliferative and anti-oxidant activity for the treatment of inflammatory conditions such as tissue edema, vascular permeability, ophthalmic itchiness scratchiness or irritation, and vascular diseases. The compounds of the present invention are also believed to be useful for treating corneal haze, and as an aid in tissue preservation. The multiple therapeutic efficacies may act in an additive or synergistic manner to reduce cellular damage.

The compounds of the present invention are useful as cytoprotective agents due to their anti-oxidant activity. The present invention also provides compounds that associate with lipid membranes, thus providing bioavailable anti-oxidant protection within lipid molecules susceptible to oxidation. The compounds of the present invention are also useful due to their anti-proliferative activity. These and other advantages of the present invention will be apparent to those skilled in the art based on the following description.

The compounds of the present invention are capable of protecting against cellular damage by a wide range of insults. Since the compounds provide this protection by decreasing free radical or oxidative damage, reducing cell proliferation, and improving site delivery, this therapy represents an improved approach to the treatment of inflammatory pathologies.

DETAILED DESCRIPTION OF INVENTION

The compounds of the present invention are of the formula (I)

wherein:

a

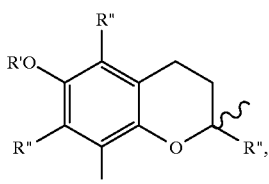

b

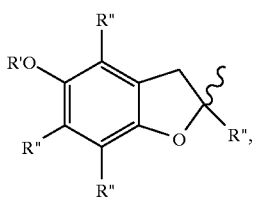

c

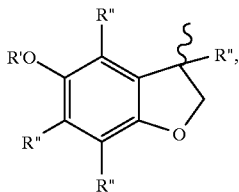

or d

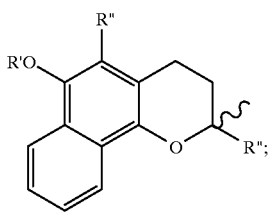

B—CH$_2$ is a NSAIA originally containing a carboxylic acid, wherein the carboxylic acid group has been reduced to form a CH$_2$ moiety, and the CH$_2$ moiety is the point of attachment;

R is C$_{1-6}$ alkyl;

R' is H, C(O)R, C(O)NR$_2$, PO$_3^-$, SO$_3^-$;

R" is H, C$_{1-6}$ alkyl;

m is 1 to 6; and p is 0 to 2.

The compounds of the present invention also include pharmaceutically acceptable salts of the compounds of formula (I).

The compounds of the present invention contain a non-steroidal anti-inflammatory agent, "B", originally having a carboxylic acid moiety, wherein the carboxylic acid moiety has lo been reduced to CH$_2$, yielding B—CH$_2$. A number of chemical classes of non-steroidal anti-inflammatory agents have been identified. The following text, the entire contents of which are hereby incorporated by reference in the present specification, may be referred to for various NSAIA chemical classes: *CRC Handbook of Eicosanoids: Prostaglandins, and Related Lipids. Volume II, Drugs Acting Via the Eicosanoids,* pages 59–133, CRC Press, Boca Raton, Fla. (1989). The NSAIA may be selected, therefore, from a variety of chemical classes including, but not limited to, fenamic acids, such as flufenamic acid, niflurnic acid and mefenamic acid; indoles, such as indomethacin, sulindac and tolmetin; phenylalkanoic acids, such as suprofen, ketorolac, flurbiprofen and ibuprofen; and phenylacetic acids, such as diclofenac. Further examples of NSAIAs are listed below:

| luxoprofen | tolfenamic acid | indoprofen |
|---|---|---|
| pirprofen | clidanac | fenoprofen |
| naproxen | fenclorac | meclofenamate |
| benoxaprofen | carprofen | isofezolac |
| aceloferac | fenbufen | etodolic acid |
| fleclozic acid | amfenac | efenamic acid |
| bromfenac | ketoprofen | fenclofenac |
| alcofenac | orpanoxin | zomopirac |
| diflunisal | pranoprofen | zaltoprofen |

The preferred compounds are those wherein "B" is selected from the naproxen, flurbiprofen or diclofenac derived derivatives. The most preferred compounds are those wherein "B" is selected from the naproxen or flurbiprofen derivatives.

With respect to the other substituents of the compounds of formula (I), the preferred compounds are those wherein:

A is

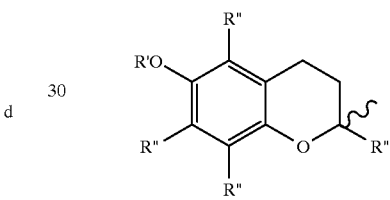

or

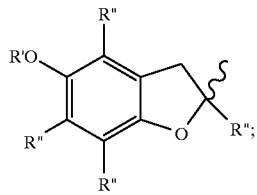

R' is H or C(O)CH$_3$;

R" is H or C$_1$–C$_3$ alkyl; and m is 1 to 4.

The most preferred compounds are those wherein:

R' is H or C(O)CH$_3$;

R" is CH$_3$; and m is 1 to 2.

The following compounds are particularly preferred:

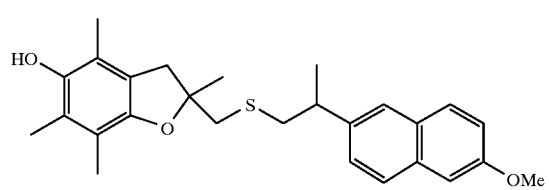

2-(5-hydroxy-2,4,5,7-tetramethyl-2,3-dihydro-benzo[1,2-b] furan-2-yl)methyl 2-(6-methoxy-naphthyl)propyl sulfide ("Compound A")

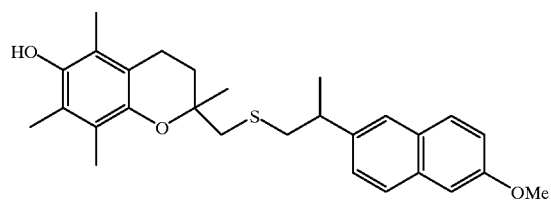

2-(5-hydroxy-2,4,5,7-tetramethyl-2,3-dihydro-2 H-benzo[1,2-b]pyran-2-yl)methyl 2-(6-methoxy-naphthyl)propyl sulfide ("Compound B")

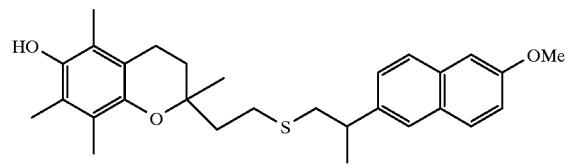

2-(5-hydroxy-2,4,5,7-tetramethyl-2,3-dihydro-2 H-benzo[1,2-b]pyran-2-yl)ethyl 2-(6-methoxy-naphthyl)propyl sulfide ("Compound C")

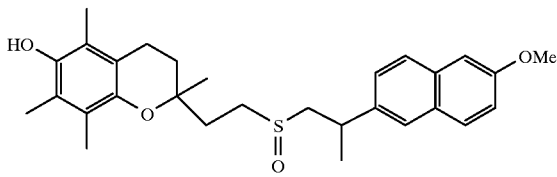

2-(5-hydroxy-2,4,5,7-tetramethyl-2,3-dihydro-2 H-benzo[1,2-b]pyran-2-yl)ethyl 2-(6-methoxy-naphthyl)propyl sulfoxide ("Compound D")

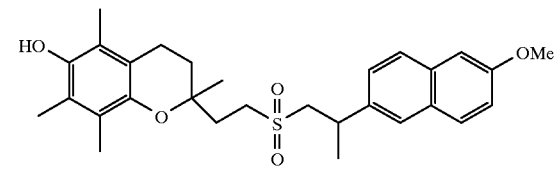

2-(5-hydroxy-2,4,5,7-tetramethyl-2,3-dihydro-2 H-benzo[1,2-b]pyran-2-yl)ethyl 2-(6-methoxy-naphthyl)propyl sulfone ("Compound E")

The compounds of the present invention may be prepared by the methods illustrated in Scheme 1 below:

Scheme 1

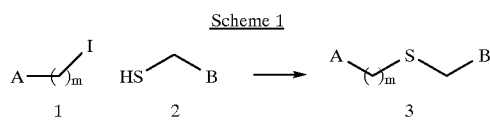

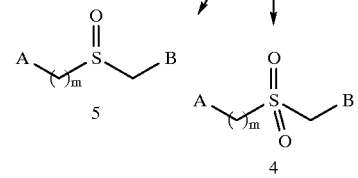

Compounds of formula (3) are prepared by first adding a solution of the thiol (2) to a solution of a base such as potassium carbonate or sodium hydride in a solvent such as tetrahydrofuran or dimethylfonnamide at a temperature from −20° C. to 10° C. for 5 to 45 minutes. A solution of the iodide (1) is then added and the reaction mixture is allowed to stir at a temperature from −20° C. to 70° C. for 1 to 10 hours. The sulfide (3) may be converted into the sulfone (4) by treating a solution of the sulfide (3) in a solvent mixture such as methanol/tetrahydrofuran or 2-propanol/water with an aqueous solution of an oxidizing agent such as oxone at a temperature from −20° C. to 30° C. for 1 to 10 hours. The sulfide (3) may be converted into the sulfoxide (5) by treating a solution of the sulfide (3 in a solvent such as methylene chloride with meta-chloroperoxybenzoic acid at a temperature from −78° C. to −30° C. for 1 to 10 hours.

The iodide (1) may be prepared as described in Scheme 2:

Scheme 2

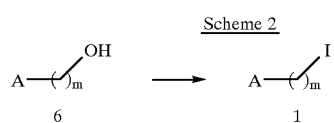

The alcohol (6) in a solvent such as tetrahydrofuran or methylene chloride is treated with triphenylphosphine, imidazole and iodine at a temperature from 20° C. to 70° C. for 1 to 10 hours.

The thiol (2) may be prepared as described in Scheme 3:

Scheme 3

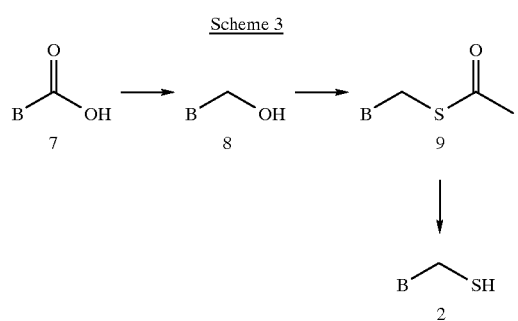

The thiol compound is prepared from the starting NSAIA by reducing the carboxylic acid with a reducing agent such as lithium aluminum hydride or diborane in a solvent such as tetrahydrofliran at a temperature from −60° C. to 50° C. for 1 to 10 hours. The resulting alcohol (8) is converted to the thiol (2) by treating a solution of the alcohol (8) and thioacetic acid in a solvent such as tetrahydrofliran or methylene chloride with a solution formned by combiniing diethylazodicarboxylate with triphenyiphosphine at a temperature from −60° C. to 50° C. for 1 to 10 hours. The resulting thioester (9 ) is cleaved to provide the thiol (2) by treating a solution of the thioester with a reducing agent such as lithium aluminum hydride in a solvent such as tetrahydrofuran at a temperature from −78° C. to 0° C. for 1 to 3 hours.

The starting materials (6) and (7) described in Schemes 2 and 3 are commercially available or may be prepared by conventional methods known to those skilled in the art. The use of certain protecting groups and deprotection steps may be necessary, as will be appreciated by those skilled in the art.

Compounds of formula (I) may exist as mixtures of stereoisomers. The preparation of the individual stereoisomers may be effected by preparing and resolving the acids (7), by known methods, and then using a single stereoisomer as starting material. The alcohols (6) may be resolved by forming esters with optically active carboxylic acids, separating the diastereomers, and then hydrolyzing the resolved diastereomers. The corresponding carboxylic acids may be resolved by forming an ester with an optically active alcohol, separating the diastereomers, and then hydrolyzing the resolved diastereomers. The carboxylic acids may also be resolved by forming an amine salt with an optically active amine. Separation by recrystallization and neutralization of the resolved carboxylic acid salt may be utilized to provide the resolved carboxylic acid. Resolution of the compound of formula (I) may also be effected using chromatographic techniques known to those skilled in the art.

Methods of synthesizing the compounds formula (I) are further illustrated by the following examples:

EXAMPLE 1

Preparation of 2-(5-hydroxy-2,4,5,7-tetramethyl-2,3-dihydro-2 H-benzo[1,2-b]pyran-2-yl)methyl 2-(6-methoxy-naphthyl)propyl sulfide ("Compound B"):

Step 1: Preparartion of 2-(6-methoxy-2-naphthyl)propanol.

To a solution of commercially available 2-(6-methoxy-2-naphthyl)propionic acid (5 grams, "g", 21.73 milimolar, ("mmol")) in anhydrous tetrahydrofuran ("THF") (100 mililiters, ("mL")) at 0° C. was added a 1 molar ("M") solution of lithium aluminum hydride ("LAH") in THF (43.47 mL). The reaction mixture was allowed to warm to room temperature and was stirred for 2 hours. A 1 M aqueous solution of HCl was added carefully followed by ethyl acetate (200 mL). The organic layer was separated, washed with a saturated solution of bicarbonate, dried (MgSO$_4$) and concentrated to yield 4 g (85%) of the title compound as a white solid. mp 88–90° C.; MS(ES) 217 (M+1). $^1$H NMR (CDCl$_3$)δ1.36 (d, 3 H, CH3), 3.06 (m, 1 H), 3.78 (d, 2 H), 3.90 (s, 3 H), 7.11–7.71 (m, 6 H).

Step 2: Preparation of 2-(6-methoxy-2-naphthyl)propyl thioacetate.

To a solution of diethylazodicarboxylate (4.03 g, 23.14 mmol) and triphenyl phosphine (6.06 g, 23.14 mmol) at 0° C. in THF (50 mL) was added 2-(6-methoxy-2-naphthyl) propan-1-ol (2.5 g, 11.57 mmol) and thioacetic acid (1.76 g, 23.14 mmol). The reaction mixture was stirred for 30 minutes before it was allowed to warm to room temperature and then stirred overnight. The reaction mixture was diluted with ethyl acetate ("EtOAc") (100 mL) and washed with water (100 mL). The organic layer was dried (MgSO$_4$) and concentrated under reduced pressure. The residue was purified by flash chromatography (silica gel, ethyl acetate-hexane (1:9)) to give 1.5 g of the title compound as an oil. $^1$H NMR (CDCl$_3$)δ1.38 (d, 3 H, CH3), 2.29 (s, 3 H, SCH3), 3.10 (m, 1 H), 3.18 (m, 2 H), 3.91 (s, 3 H, OCH3), 7.11–7.72 (m, 6 H).

Step 3: Preparation of 2-(6-methoxy-2-naphthyl)propane thiol.

Methyl-2-(6-methoxy-2- naphthyl)thiopropanoate (1.5 g, 5.77 mmol) was dissolved in ethyl ether (100 mL) and cooled down to 0° C. To this solution, a 1 M solution of LAH in ether (13.76 mL) was added dropwise. The reaction mixture was warmed at refluxed for 3 hours. The reaction was quenched by adding ethyl acetate and 1 M aqueous HCl. The organic layer was separated, dried (MgSO$_4$), and concentrated under reduced pressure. The residue was purified by flash chromatography (silica gel, ethyl acetate-hexane, 2:8) to provide the title compound as a solid. mp 40–42 0° C. $^1$H NMR (CDCl$_3$)δ1.25 (dd, 1 H, SH), 1.42 (d, 3 H, CH3), 2.70–2.90 (m, 2 H), 3.10 (m, 1 H), 7.11–7.71 (m, 6 H).

Step 4: Preparation of methyl -2-(6-tetrabutyldimethylsilyloxy-2,5,7,8-tetramethylchroman) carboxylate.

To a solution of the commercially available trolox (5 g, 19.97 mmol) in methanol (50 mL) was added 2 drops of concentrated sulfuric acid. The reaction mixture was stirred at reflux temperature for 4 hours and then the volatiles were evaporated. The residue was dissolved in THF (50 mL), tert-butyl-dimethylsilyl chloride ("TBDMSCl") (7.13 g, 47.30) and imidazole (6.4 g, 94.69 mmol) were added respectively and then the reaction mixture was stirred at room temperature for 4 hours. The reaction mixture was diluted with ethyl acetate (200 mL) and washed with 0.1 M aqueous HCl. The organic layer was dried (MgSO$_4$), and concentrated under reduced pressure. The residue was purified by flash chromatography (silica gel , hexane-ethyl acetate (9:1)) to give 6 g (83%) of the title compound as an oil. $^1$H NMR (CDCl$_3$) δ0.01 (s, 6 H), 0.93 (s, 9 H), 1.49 (s, 3 H), 1.80 (m, 1 H), 1.91 (s, 3 H), 2.00 (s, 3 H), 2.05 (s, 3 H), 2.70–2.90 (m, 3 H), 3.56 (s, 3 H, OCH3).

Step 5: Preparation of 2-hydroxymethyl-6-tetrabutyldimethylsilyloxy-2,5,7,8-tetramethylchroman.

Methyl-2-(6-tetrabutyldimethylsilyloxy-2,5,7,8-tetramethylchroman) carboxylate (8 g, 21.16 mmol) was dissolved in dry THF and cooled to 0° C. To this cold solution was added a 1.0 M solution of LAH in ether (42 mL). The reaction mixture was stirred 30 min at 0° C., allowed to warm to room temperature and stirred for 1 h the reaction was quenched by adding ethyl acetate followed by a 1 M aqueous solution of HCl. The combined organic layers were dried (MgSO$_4$) and concentrated under reduced pressure to give 6 g (78%) of the title compound as an oil. $^1$H NMR (CDCl$_3$) δ0.01 (s, 6 H), 0.95 (s, 9 H), 1.49 (s, 3 H), 1.65 (m, 1 H), 1.85 (m, 1 H), 1.90 (m, 9 H), 2.50 (m, 2 H), 3.50 (m, 2 H).

Step 6: Preparation of 2-(5-hydroxy-2,4,5,7-tetramethyl-2, 3-dihydro-2 H-benzo[1,2-b]pyran-2-yl)methyl 2-(6-methoxy-naphthyl)propyl sulfide.

6-tetrabutyldimethylsilyloxy-2,5,7,8-tetramethylchroman-2-methanol (1 g, 2.85 mmol) was dissolved in THF (50 mL). To this solution was added triphenyl phosphine ("PPh3") (1.12 g, 4.28 mmol), iodide (0.87 g, 3.42 mmol) and imidazole (0.29 g, 4.28 mmol). The reaction mixture was heated at 60° C. for 2 hours. The heterogeneous solution was cooled to ambient temperature, diluted with ethyl acetate (200 mL) and washed with 1 M aqueous solution of HCl. The combined organic layers were dried (MgSO$_4$) and concentrated under reduced pressure. The oily residue obtained was dissolved in 20 mL of dimethyl formate ("DMF") and added to a cold solution (ice bath) of 2-(6-Methoxy-2-naphthyl)propane thiol (0.54 g, 2.30 mmol) and sodium hydride ("NaH") (0.11 g, 2.76 mmol ) in DMF (50 mL). The reaction mixture was allowed to warm to 60° C. and stirred for 4 hours. DMF was evaporated and then the residue was dissolved in ethyl acetate (100 mL) and washed with a 1 M aqueous solution of HCl. The organic layer was dried and the residue was purified by flash chromatography to give 0.5 g (38%) of the title compound as an oil. MS(CI) (M+1) 451 $^1$H NMR (CDCl$_3$) 1.31 (m, 3 H+1 H) 1.41 (d, 3 H), 1.75 (m, 1 H), 1.90 (m, 1 H), 2.12 (m, 9 H), 2.5–3.1 (m, 6 H), 3.90 (s, 3 H, OCH3), 4.2 (s, 1 H, OH), 7.1–7.7 (6 H). Analyzed for C$_{28}$ H$_{34}$O$_3$S 0.2 H$_2$O: C74.04, H:7.63 found C: 73.93, H: 7.67

EXAMPLE 2

Preparation of 2-(5-hydroxy-2,4,5,7-tetramethyl-2,3-dihydro-2 H-benzo[1,2-b]pyran-2-yl)ethyl-2-(6-methoxy-naphthyl)propyl sulfide:

Step 1: Preparation of methyl-2-(6-hydroxy-2,5,7,8-tetramethylchroman) acetate.

To a solution of the 2-(6-hydroxy-2,5,7,8-tetramethylchroman) acetic acid (10 g, 37.87 mmol) in methanol (50 mL) was added 2 drops of concentrated sulfuric acid. The reaction mixture was warmed at reflux for 4 hours and then the volatiles were evaporated to give 10 g (95%) of the title compound as an oil. $^1$H NMR (CDCl$_3$) δ1.41(s, 3 H), 1.80–2.10 (m, 3 H), 2.10 (s, 3 H), 2.15 (s, 3 H), 2.15 (s, 3 H), 2.6 (m, 3 H), 3.68 (s, 3 H), 4.3 (s, 1 H, OH).

Step 2: Preparation of methyl 2-(6-tetrabutyldimethylsilyloxy-2,5,7,8-tetramethylchroman) acetate To a solution of methyl-2-(6-hydroxy-2,5,7,8-tetramethylchroman) acetate (10 g, 35.97 mmol) dissolved in THF (50 mL) was added TBDMSC1 (21.8 g, 0.14 mol) and imidazole (19.6 g, 0.28 mol). The reaction mixture was stirred at room temperature for 4 hours, diluted with ethyl acetate (200 mL) and washed with 0.1 M aqueous solution of HCl. The organic layer was dried (MgSO$_4$), concentrated under reduced pressure and the residue was purified by flash chromatography (silica gel, hexane-ethyl acetate (9:1)) to give 13 g (96%) of the title compound as an oil. $^1$H NMR (CDCl$_3$) δ0.01 (s, 6 H), 1.22 (s, 9 H), 1.41 (s, 3 H), 1.8–2.1 (m, 2 H), 0.91 (m, 9 H), 2.60 (m, 4 H), 3.68 (s, 3 H).

Step 3: Preparation of 2-(6-tetrabutyldimethylsilyloxy-2,5,7,8-tetrarnethylchroman) ethanol Methyl -2-(6-tetrabutyldimethylsilyloxy-2,5,7,8-tetramethylchroman) acetate (5 g, 12.46 mmol) was dissolved in dry THF and cooled to 0° C. To this cold solution was added a 0.1 M solution of LAH in ether (15 mL). The reaction mixture was stirred 30 min at 0° C., allowed to warm to room temperature and stirred for 1 hour. The reaction was quenched by the addition of EtOAc followed by 1 M aqueous HCl. The organic layer dried (MgSO$_4$) and concentrated under reduced pressure to give 3.7 g (77%) of the title compound as an oil. $^1$H NMR (CDCl$_3$) δ0.01 (s, 6 H), 1.04 (s, 9 H), 1.27 (s, 3 H), 1.70–1.95 (m, 3 H), 2.05 (m, 9 H), 2.65 (m, 3 H), 3.90 (m, 2 H).

Step 4: Preparation of 2-(6-tetrabutyldimethylsilyloxy-2,5,7,8-tetramethylchroman) iodoethane A solution of 2-(6-tetrabutyldimethylsilyloxy-2,5,7,8-tetramethylchroman) iodoethane (11 g, 31.25 mmol) in THF (100 mL) was added to a solution of PPh3 (12.3 g, 46.87 mmol), iodide (9.52 g, 37.5 mmol) and imidazole (3.19 g, 46.87 mmol). The reaction mixture was warmed at 60° C. for 2 hours. The heterogeneous solution was cooled to ambient temperature, diluted with EtOAc (200 mL) and then washed with 0.1 M aqueous solution of HCl. The organic layers were dried (MgSO$_4$) and concentrated under reduced pressure. The residue was purified by flash chromatography to give 8 g (74%) of the title compound as an oil. MS(CI) (M+1) 475 $^1$H NMR (CDCl$_3$) δ0.01 (s, 6 H), 1.04 (s, 9 H), 1.24 (s, 3 H), 1.77 (m, 2 H),), 2.05 (m, 9 H), 2.1–2.4 (m, 2 H), 2.57 (m, 2 H), 3.30 (m, 2 H).

Step 5: Preparation of 2-(5-hydroxy-2,4,5,7-tetramethyl-2,3-dihydro-2 H-benzo[1,2-b]pyran-2-yl)ethyl 2-(6-methoxy-naphthyl)propyl sulfide.

To a cold solution of 2-(6-methoxy-2-naphthyl)propane-1-thiol (0.75 g, 3.21 mmol) in DMF (50 mL) was added NaH (0.15 g, 3.85 mmol). The reaction mixture was stirred for 20 minutes and then 2-(6-tetrabutyldimethylsilyloxy-2,5,7,8-tetramethylchroman) iodoethane (2.21 g, 3.85 mmol) was added. The reaction mixture was allowed to warm to 50° C. and was stirred for 4 hours. DMF was evaporated under vacuum and the residue was dissolved in dichloromethane (50 mL) and washed with a 1 M aqueous solution of HCl. The organic layer was separated and dried. To the residue was added a 1 M solution of tetrabutylammonium fluoride ("TBAF") in dichloromethane (6.42 mL) and the reaction mixture was stirred for 2 hours. The reaction mixture was then washed with water, dried (MgSO$_4$) and concentrated under reduced pressure. The residue was purified by flash chromatography (silica gel, ethyl acetate-hexane (1:1)) to give 1 g (45%) of the title compound as a white-yellow solid. mp: 97–99° C. MS(CI) 465 (M+1) $^1$H NMR (CDCl$_3$) δ1.19 (s, 3 H), 1.42 (d, 3 H), 1.7–1.9 (m, 5 H),), 2.05 (m, 9 H, 3CH3), 2.5–3.1 (m, 6 H), 3.90 (s, 3 H), 4.2 (s, 1 H), 7.1–7.7 (m, 6 H). Analysis calculated for C$_{29}$ H$_{36}$O$_3$S.0.3 H$_2$O: C74.10, H:7.85 found C: 74.10, H: 7.86

EXAMPLE 3

Preparation of 2-(5-hydroxy-2,4,5,7-tetramethyl-2,3-dihydro-2 H-benzo[1,2-b]pyran-2-yl)ethyl 2-(6-methoxy-naphthyl)propyl sulfone.

To a cold solution of 2-(6-methoxy-2-naphtalene)ethane thiol (0.75 g, 3.21 mmol) in DMF (50 mL) was added NaH (0.15 g, 3.85 mmol). The reaction mixture was stirred for 20 minutes and then 2-(6-tetrabutyldimethylsilyloxy-2,5,7,8-tetramethylchroman) iodoethane (2.21 g, 3.85 mmol) was added. The reaction mixture was allowed to warm to 50° C. and was stirred for 4 hours. The solvent was evaporated under vacuum and the residue was dissolved in dichloromethane (50 mL), and washed with 0.1 M aqueous solution of HCl. The solvent was evaporated and replaced by a mixture of methanol-tetrahydrofuran (20 mL–5 mL). To this stirring solution was added a solution of oxone (2.95 g, 4.82 mmol) in water (5 mL). The reaction mixture was stirred for 1 hour and then the volatiles were evaporated. The residue was dissolved in dichloromethane (50 mL) and washed with 1 M aqueous solution of HCl. The organic layer was separated and dried. To this residue was added a 1 M solution of TBAF in dichloromethane (6.42 mL) and stirred for 2 hours. The reaction mixture was washed with water, dried (MgSO$_4$) and concentrated under reduced pressure. The residue was purified by flash chromatography (silica gel, acetone-hexane (1:1)) to give 140 mg (6%) of the title compound as a white solid. mp: 130–132° C. MS(CI) 497 (M+1) $^1$H NMR (CDCl$_3$) δ0.94 (s, 3 H), 1.51 (m, 7 H), 2.05 (m, 9 H, 3CH3), 2.5 (m, 2 H), 2.70 (m, 2 H), 3.30 (m, 2 H), 3.6 (m, 1 H), 3.89 (s, 3 H), 4.2 (s, 1 H), 7.1–7.7 (m, 6 H). Analyzed for C$_{29}$ H$_{36}$O$_5$S: calculated for C70.13, H:7.31 found C: 70.20, H: 7.40.

The compounds of formula (I) may be contained in various types of pharmaceutical compositions, in accordance with formulation techniques known to those skilled in the art. For example, the compounds may be included in tablets, capsules, solutions, creams, suspensions and other dosage forms adapted for oral administration; solutions and suspensions adapted for topical or parenteral use; and suppositories for rectal use.

The present invention is particularly directed to the provision of compositions adapted for treatment of oxidative stress or inflammatory conditions. The compositions of the present invention will include one or more compounds of formula (I) and a pharmaceutically acceptable vehicle for said compound(s). Various types of vehicles may be utilized. Suspensions may be preferred for compounds of formula (I) which are relatively insoluble in water.

An appropriate buffer system (e.g., sodium phosphate, sodium acetate or sodium borate) may be added to prevent pH drift under storage conditions.

Some of the compounds of formula (I) may have limited solubility in water and therefore may require a surfactant or other appropriate co-solvent in the composition. Such co-solvents include: polyethoxylated castor oils, HCO-40, Polysorbate 20, 60 and 80; Pluronic® F-68, F-84 and P-103 (BASF Corp., Parsippany N.J., USA); cyclodextrin; or other agents known to those skilled in the art. Such co-solvents are typically employed at a level of from 0.01 to 2 percent weight/volume ("% w/v").

The pharmaceutical compositions containing one or more compound of formula (I) may be used to treat patients afflicted with or prone to various types of cellular damage. In particular, these compositions may be used for inflammation where prostaglandins, leukotrienes, cytokines, and chemokines are known to participate. The concentrations of the compounds in the compositions will depend on various factors, including the nature of the condition to be treated with the compositions. However, the compositions may contain one or more of the compounds of the present invention in a concentration of from about 0.001 to about 5% w/v, for topical administration.

The route of administration (e.g., topical, parenteral or oral) and the dosage regimen will be determined by skilled clinicians, based on factors such as the exact nature of the condition being treated, the severity of the condition, the age and general physical condition of the patient, and so on.

As indicated above, compounds of formula (I) may be used to treat ocular inflammation at the cellular level and represents a particularly important aspect of the invention. The compounds are also useful in treating post-surgical complications resulting from ocular surgery. Treatment of the patient pre- or post-surgery with compounds of formula (I) may alleviate such conditions as tissue edema, neovascularization, conjunctiva swelling and congestion, corneal haze and cataract formation.

As indicated above, compound of formula (a) may also be used to preserve organs or tissue during the interim period between excision and transplantation. The compound are particularly useful in preserving corneas for transplantation.

As indicated above, compounds of formula (I) may also be used to prevent or reduce damage to vascular tissues at the cellular level. As used herein, "vascular inflammatory pathologies" refers to inflammation of the vasculature resulting from oxidation-mediated stress or stress mediated by other biochemical agents, such as cyclooxygenase or lipoxygenase inflammatory products. Vascular inflammatory pathologies which may be treated include, but are not limited to, atherosclerosis, thrombosis, hypercholesterolemia, congestive heart disease, stroke and unstable angina. The compounds may also be used as an adjunct to cardiac or brain surgery. The compounds may be used for acute treatment of temporary conditions, or may be administered chronically, especially in the case of degenerative disease. The compounds may also be used prophylactically to treat high-risk heart disease patients.

The compounds and compositions of the present invention will be used in a therapeutically effective amount. As used herein, a "therapeutically effective amount" is that amount required to prevent, reduce or ameliorate cellular inflammation, oxidation or pathological proliferation. The doses utilized for any of the above-described purposes will generally be from about 0.01 to about 100 milligrams per kilogram of body weight (mg/kg). When topically administered they will be dosed one to four times per day.

The compounds of the present invention are further illustrated by the following biological assay examples.

EXAMPLE 4

The antioxidant activity of representative compounds of the present invention, as compared with Vitamin E, is presented in Table 1 below. Ability to inhibit lipid peroxidation was measured in bovine heart membranes using a modification of the method described by Parinandi et al (*Arch Biochem Biophys*, volume 28, pages 45–52, 1990). Aliquots of a bovine membrane preparation were incubated in the presence or absence of the test compound at 37° C. for 30 minutes. Peroxidation was then induced by the addition of $Fe^{+2}$/ascorbate, with continued incubation for 15 minutes at room temperature. Anti-oxidant activity was assayed by quantifying thiobarbituric acid-reactive substance formation at 540 nm. Percent inhibition of thiobarbituric acid-reactive substance formation by the test compound was calculated relative to untreated control preparations.

TABLE 1

| Compound | Membrane Oxidation $IC_{50}$ ($\mu M$) |
| --- | --- |
| Compound B | 4.3 |
| Compound C | 5.1 |
| Vitamin E | 5173 |

EXAMPLE 5

A respretentative compound of the present invention, Compound E, was evaluated for its ability to interact with phospholipids in monolayers and bilayers. The procedures employed to evaluate lipid interaction with lipophilic agents have been described elsewhere (*Biochemistry*, volume 34, pages 7271–7281 (1995), and *Langmuir*, volume 8, pages 563–570 (1992)). From these studies, it was apparent that Compound E exhibits minimal intrinsic surface-active properties. In spite of its low endogenous surface-activity, Compound E partitioned from the aqueous solution into the phospholipid monolayer at initial packing densities exceeding those believed to exist in membranes. This finding supports an energetically favorable interaction between phospholipids and representative compounds of the present invention (e.g., Compound E). Assessment of Compound E's interaction with phospholipids in a liquid-expanded monolayer state also indicated eutectic-type phase diagrams with a solubility approaching 20 to 30 mole percent in dipalmitoylphosphatidylcholine. Additional evidence for its ability to interact with phospholipids was obtained by an alteration in the fluorescence of pyrene-labeled phospholipid in a liquid-crystalline phospholipid bilayer.

EXAMPLE 6

DNA synthesis inhibition, a measure of anti-proliferative effect, by representative compounds of the present invention is shown in Table 2 below. The compounds were solubilized in Tetronic-304, then diluted separately into filtered sterilized culture medium to achieve a final drug concentration of 1.0 to 25 μM. the final concentration of Tetronic-304 in the assay was 0.05% w/v. Medium containing either compound or vehicle control, was then incubated with cultured HMVEC-lung cells for 18 hours at which time, ³H-thymidine was added and the cells were subsequently re-incubated for an additional 6 hours. The reaction was stopped by the addition of cold trichloroacetic acid ("TCA") and DNA synthesis was assessed by quantifying the amount of tritium incorporation into an acid insoluble product. Prior to initiating the experiment, no attempt was made to synchronize these cells.

TABLE 2

| Compound | Inhibition of DNA Sythesis IC$_{50}$ (μM) |
| --- | --- |
| Compound B | 16.6 |
| Compound C | 23.1 |
| Compound E | 3.4 |

What is claimed is:

1. A compound of formula (I):

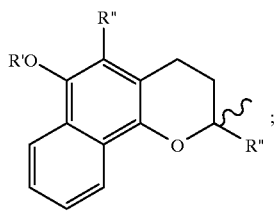

wherein:

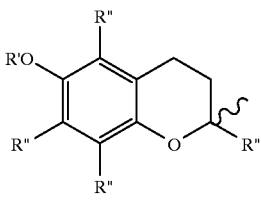

B is a NSAIA originally containing a carboxylic acid, wherein the carboxylic acid group has been reduced to form a $CH_2$ moiety, and the $CH_2$ moiety is the point of attachment;

R is $C_{1-6}$ alkyl;

R' is H, C(O)R, C(O)NR$_2$, PO$_3^-$, SO$_3^-$;

R" is H, $C_{1-6}$ alkyl;

m is 1 to 6; and p is 0 to 2; or a pharmaceutically acceptable salt thereof.

2. A compound according to claim 1, wherein:

A is

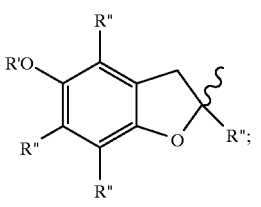

R' is H or C(O)CH$_3$;

R" is H or $C_1$–$C_3$ alkyl; and m is 1 to 4.

3. A compound according to claim 2, wherein:

R' is H or C(O)CH$_3$;

R" is CH$_3$; and m is 1 to 2.

4. A compound according to claim 1, wherein the non-steroidal anti-inflammatory agent is selected from the group consisting of: fenamic acids; indoles; phenylalkanoic acids.

5. A compound according to claim 4, wherein:

A is

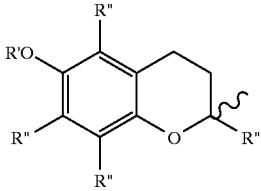

-continued or

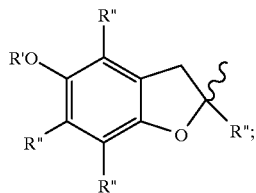

R' is H or C(O)CH$_3$;
R" is H or C$_1$–C$_3$ alkyl; and
m is 1 to 4.

6. A compound according to claim 5, wherein:
R' is H or C(O)CH$_3$;
R" is CH$_3$; and
m is 1 to 2.

7. A compound according to claim 1, wherein the NSAIA is selected from the group consisting of:
loxoprofen; tolfenamic acid; indoprofen; pirprofen; clidanac; fenoprofen; naproxen; fenclorac; meclofenamate; benoxaprofen; carprofen; isofezolac; aceloferac; fenbufen; etodolic acid; fleclozic acid; amfenac; efenamic acid; bromfenac; ketoprofen; fenclofenac; alcofenac; orpanoxin; zomopirac; diflunisal; flufenamic acid; niflumic acid; mefenamic acid; pranoprofen; zaltoprofen; indomethacin; sulindac; tolmetin; suprofen; ketorolac; flurbiprofen; ibuprofen; and diclofenac.

8. A compound according to claim 7, wherein:
A is

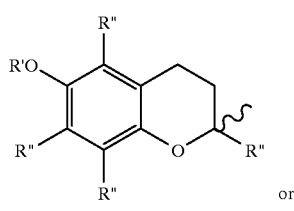

or

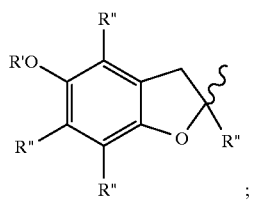

R' is H or C(O)CH$_3$;
R" is H or C$_1$–C$_3$ alkyl; and
m is 1 to 4.

9. A compound according to claim 8, wherein:
R' is H or C(O)CH$_3$;
R" is CH$_3$; and
m is 1 to2.

10. A compound according to claim 1, wherein the non-steroidal anti-inflammatory agent is selected from the group consisting of naproxen, flurbiprofen and diclofenac.

11. A compound according to claim 8, wherein the non-steroidal anti-inflammatory agent is selected from the group consisting of naproxen, flurbiprofen and diclofenac.

12. A compound according to claim 9, wherein the non-steroidal anti-inflammatory agent is selected from the group consisting of naproxen, flurbiprofen and diclofenac.

13. A compound according to claim 1, wherein the compound has the following formula:

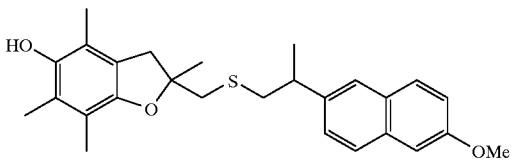

2-(5-hydroxy-2,4,5,7-tetramethyl-2,3-dihydro-benzo[1,2-b]furan-2-yl)methyl 2-(6-methoxy-naphthyl)propyl sulfide;

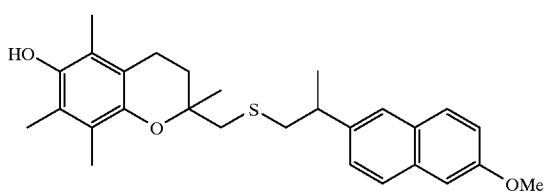

2-(5-hydroxy-2,4,5,7-tetramethyl-2,3-dihydro-2 H-benzo[1,2-b]pyran-2-yl)methyl 2-(6-methoxy-naphthyl)propyl sulfide;

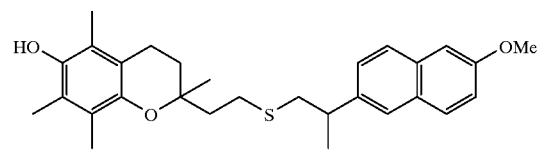

2-(5-hydroxy-2,4,5,7-tetramethyl-2,3-dihydro-2 H-benzo[1,2-b]pyran-2-yl)ethyl 2-(6-methoxy-naphthyl)propyl sulfide;

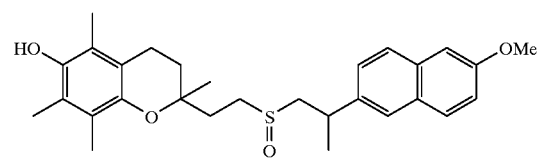

2-(5-hydroxy-2,4,5,7-tetramethyl-2,3-dihydro-2 H-benzo[1,2-b]pyran-2-yl)ethyl 2-(6-methoxy-naphthyl)propyl sulfoxide; and

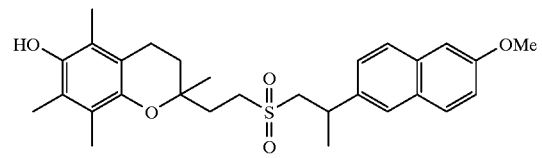

2-(5-hydroxy-2,4,5,7-tetramethyl-2,3-dihydro-2 H-benzol[1,2-b]pyran-2-yl)ethyl 2-(6-methoxy-naphthyl)propyl sulfone.

14. A pharmaceutical composition for preventing or alleviating damage to mammalian tissues comprising an therapeutically effective amount of a compound of the following formula (I):

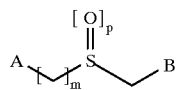
(I)

wherein:

A is

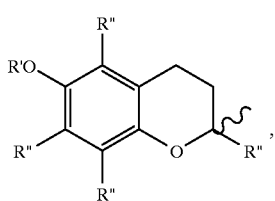
a

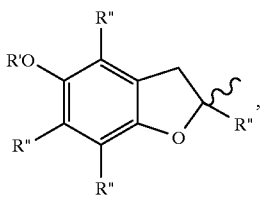
b

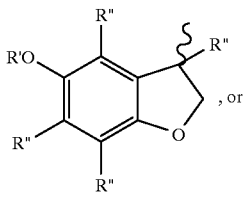
c, or

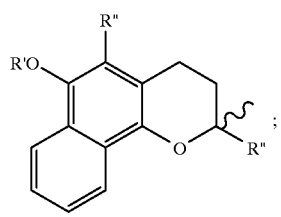
d;

B is a NSAIA originally containing a carboxylic acid, wherein the carboxylic acid group has been reduced to form a CH$_2$ moiety, and the CH$_2$ moiety is the point of attachment;

R is C$_{1-6}$ alkyl;

R' is H, C(O)R, C(O)NR$_2$, PO$_3^-$, SO$_3^-$;

R" is H, C$_{1-6}$ alkyl;

m is 1 to 6; and p is 0 to 2; or a pharmaceutically acceptable salt thereof.

15. A composition according to claim 14, wherein:

A is

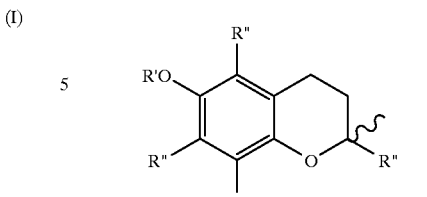
or

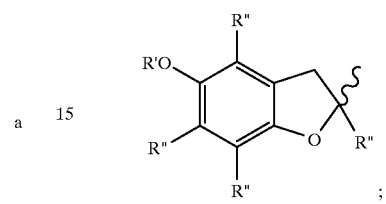
;

R' is H or C(O)CH$_3$;

R" is H or C$_1$–C$_3$ alkyl; and m is 1 to 4.

16. A composition according to claim 15, wherein:

R' is H or C(O)CH$_3$;

R" is CH$_3$; and m is 1 to 2.

17. A composition according to claim 14, wherein the non-steroidal anti-inflammatory agent is selected from the group consisting of: fenamic acids; indoles; phenylalkanoic acids.

18. A composition according to claim 17, wherein:

A is

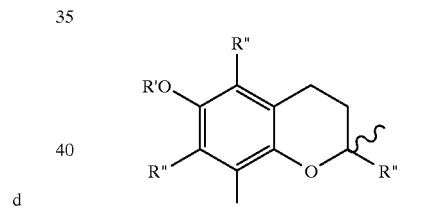
or

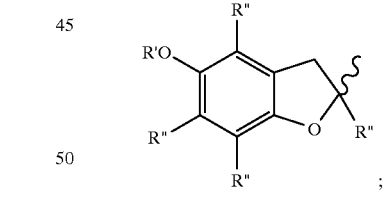
;

R' is H or C(O)CH$_3$;

R" is H or C$_1$–C$_3$ alkyl; and m is 1 to 4.

19. A composition according to claim 18, wherein:

R' is H or C(O)CH$_3$;

R" is CH$_3$; and m is 1 to 2.

20. The composition according to claim 14, wherein the NSAIA is selected from the group consisting of:

loxoprofen; tolfenamic acid; indoprofen; pirprofen; clidanac; fenoprofen; naproxen; fenclorac; meclofenamate;

benoxaprofen; carprofen; isofezolac; aceloferac; fenbufen; etodolic acid; fleclozic acid; amfenac; efenamic acid; bromfenac; ketoprofen; fenclofenac; alcofenac; orpanoxin; zomopirac; diflunisal; flufenamic acid; niflumic acid; mefenamic acid; pranoprofen; zaltoprofen; indomethacin; sulindac; tolmetin; suprofen; ketorolac; flurbiprofen; ibuprofen; and diclofenac.

21. A composition according to claim 20, wherein:

A is

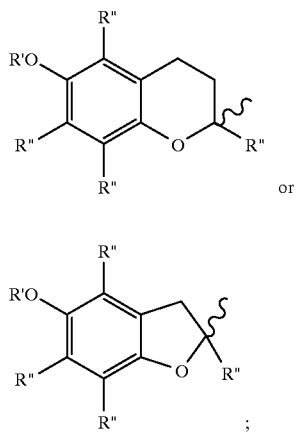

R' is H or C(O)CH$_3$;

R" is H or C$_1$–C$_3$ alkyl; and m is 1 to 4.

22. A composition according to claim 21, wherein:

R' is H or C(O)CH$_3$;

R" is CH$_3$; and m is 1 to 2.

23. A composition according to claim 20, wherein the non-steroidal anti-inflammatory agent is selected from the group consisting of naproxen, flurbiprofen and diclofenac.

24. A composition according to claim 21, wherein the non-steroidal anti-inflammatory agent is selected from the group consisting of naproxen, flurbiprofen and diclofenac.

25. A composition according to claim 22, wherein the non-steroidal anti-inflammatory agent is selected from the group consisting of naproxen, flurbiprofen and diclofenac.

26. A composition according to claim 14, wherein the compound has the following formula:

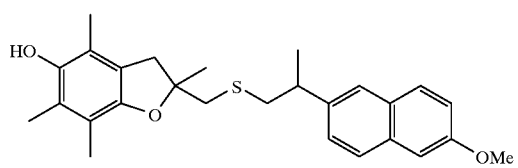

2-(5-hydroxy-2,4,5,7-tetramethyl-2,3-dihydro-benzo[1,2-b]furan-2-yl)methyl 2-(6-methoxy-naphthyl)propyl sulfide;

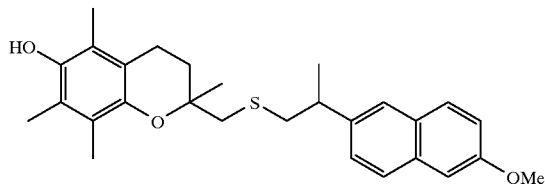

2-(5-hydroxy-2,4,5,7-tetramethyl-2,3-dihydro-2 H-benzo[1,2-b]pyran-2-yl)methyl 2-(6-methoxy-naphthyl)propyl sulfide;

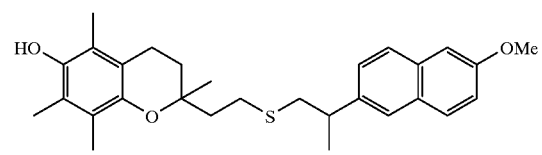

2-(5-hydroxy-2,4,5,7-tetramethyl-2,3-dihydro-2 H-benzo[1,2-b]pyran-2-yl)ethyl 2-(6-methoxy-naphthyl)propyl sulfide;

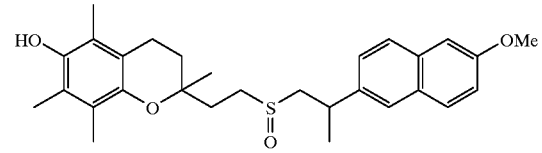

2-(5-hydroxy-2,4,5,7-tetramethyl-2,3-dihydro-2 H-benzo[1,2-b]pyran-2-yl)ethyl 2-(6-methoxy-naphthyl)propyl sulfoxide; and

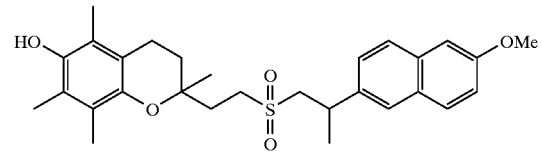

2-(5-hydroxy-2,4,5,7-tetramethyl-2,3-dihydro-2 H-benzo[1,2-b]pyran-2-yl)ethyl 2-(6-methoxy-naphthyl)propyl sulfone.

27. A method of preventing or alleviating damage to mammalian tissues which comprises administering a therapeutically effective amount of a composition comprising a compound of the following formula (I):

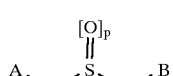

(I)

wherein:

A is

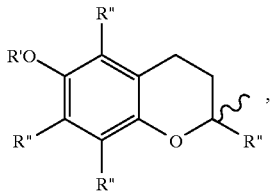

a

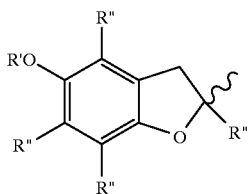

b

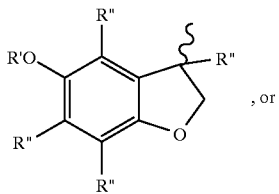, or c

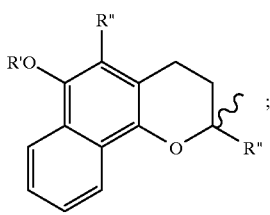;

d

B is a NSAIA originally containing a carboxylic acid, wherein the carboxylic acid group has been reduced to form a $CH_2$ moiety, and the $CH_2$ moiety is the point of attachment;

R is $C_{1-6}$ alkyl;

R' is H, C(O)R, C(O)$NR_2$, $PO_3^-$, $SO_3^-$;

R" is H, $C_{1-6}$ alkyl;

m is 1 to 6; and p is 0 to 2; or a pharmaceutically acceptable salt thereof.

28. A method according to claim 27, wherein:

A is

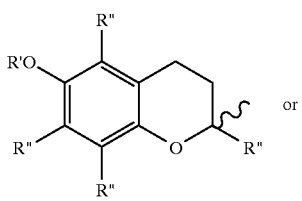 or

-continued

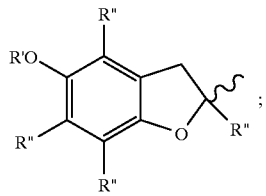;

R' is H or C(O)$CH_3$;

R" is H or $C_1$–$C_3$ alkyl; and m is 1 to 4.

29. A method according to claim 28, wherein:

R' is H or C(O)$CH_3$;

R" is $CH_3$; and m is 1 to 2.

30. A method according to claim 27, wherein the non-steroidal anti-inflammatory agent is selected from the group consisting of: fenamic acids; indoles; phenylalkanoic acids.

31. A method according to claim 30, wherein:

A is

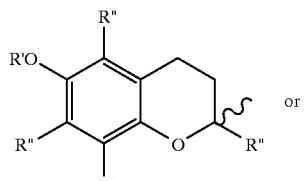 or

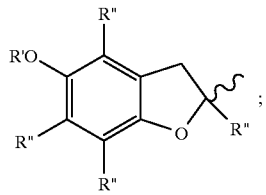;

R' is H or C(O)$CH_3$;

R" is H or $C_1$–$C_3$ alkyl; and m is 1 to 4.

32. A method according to claim 31, wherein:

R' is H or C(O)$CH_3$;

R" is $CH_3$; and m is 1 to 2.

33. A method according to claim 27, wherein the NSAIA is selected from the group consisting of:

loxoprofen; tolfenamic acid; indoprofen; pirprofen; clidanac; fenoprofen; naproxen; fenclorac; meclofenamate; benoxaprofen; carprofen; isofezolac; aceloferac; fenbufen; etodolic acid; fleclozic acid; amfenac; efenamic acid; bromfenac; ketoprofen; fenclofenac; alcofenac; orpanoxin; zomopirac; diflunisal; flufenamic acid; niflumic acid; mefenamic acid; pranoprofen; zaltoprofen; indomethacin; sulindac; tolmetin; suprofen; ketorolac; flurbiprofen; ibuprofen; and diclofenac.

34. A method according to claim 33, wherein:
A is

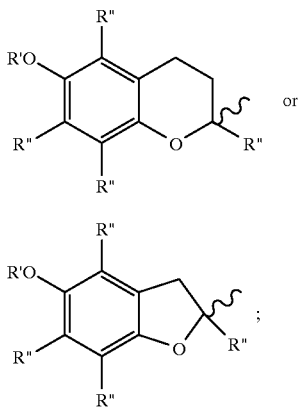

R' is H or C(O)CH$_3$;
R" is H or C$_1$–C$_3$ alkyl; and
m is 1 to 4.

35. A method according to claim 34, wherein:
R' is H or C(O)CH$_3$;
R" is CH$_3$; and
m is 1 to 2.

36. A method according to claim 27, wherein the non-steroidal anti-inflammatory agent is selected from the group consisting of naproxen, flurbiprofen and diclofenac.

37. A method according to claim 34, wherein the non-steroidal anti-inflanmmatory agent is selected from the group consisting of naproxen, flurbiprofen and diclofenac.

38. A method according to claim 35, wherein the non-steroidal anti-inflammatory agent is selected from the group consisting of naproxen, flurbiprofen and diclofenac.

39. A method according to claim 27, wherein the compound has the following formula:

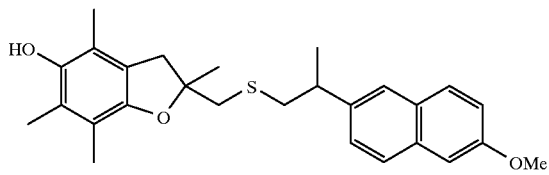

2-(5-hydroxy-2,4,5,7-tetramethyl-2,3-dihydro-benzo[1,2-b]furan-2-yl)methyl 2-(6-methoxy-naphthyl)propyl sulfide;

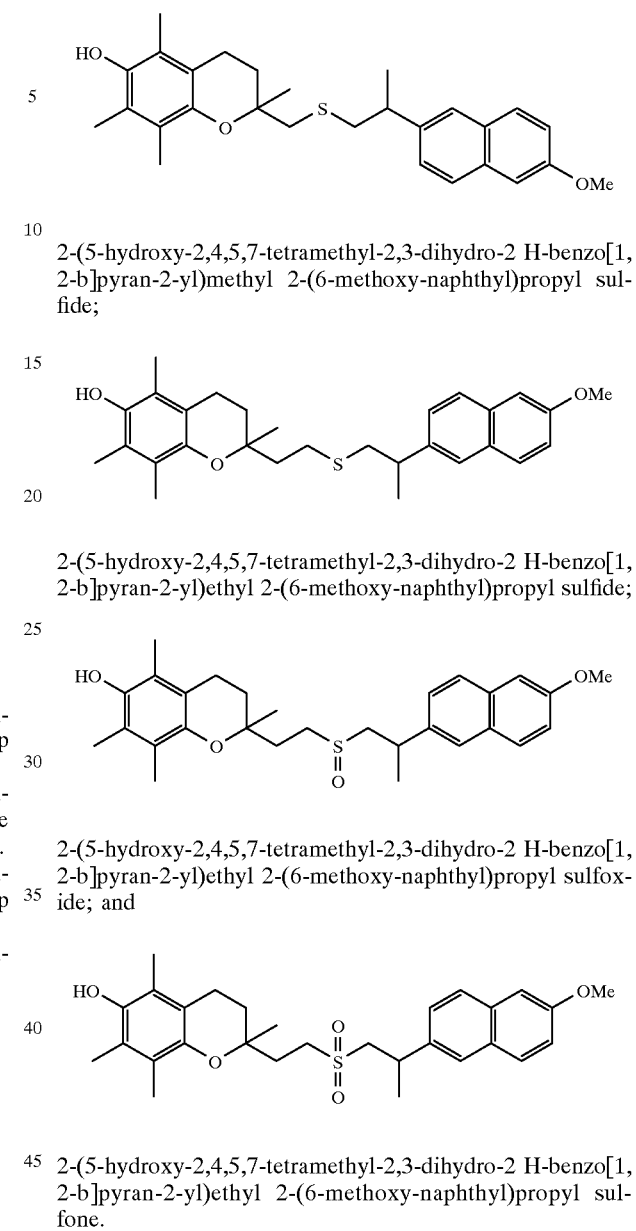

2-(5-hydroxy-2,4,5,7-tetramethyl-2,3-dihydro-2 H-benzo[1,2-b]pyran-2-yl)methyl 2-(6-methoxy-naphthyl)propyl sulfide;

2-(5-hydroxy-2,4,5,7-tetramethyl-2,3-dihydro-2 H-benzo[1,2-b]pyran-2-yl)ethyl 2-(6-methoxy-naphthyl)propyl sulfide;

2-(5-hydroxy-2,4,5,7-tetramethyl-2,3-dihydro-2 H-benzo[1,2-b]pyran-2-yl)ethyl 2-(6-methoxy-naphthyl)propyl sulfoxide; and 2-(5-hydroxy-2,4,5,7-tetramethyl-2,3-dihydro-2 H-benzo[1,2-b]pyran-2-yl)ethyl 2-(6-methoxy-naphthyl)propyl sulfone.

* * * * *